United States Patent [19]
Mirsch, II et al.

[11] Patent Number: 6,121,041
[45] Date of Patent: *Sep. 19, 2000

[54] USE OF MICROORGANISMS FOR DECELLULARIZING BIOPROSTHETIC TISSUE

[75] Inventors: M. William Mirsch, II, Roseville; Richard F. Schroeder, Oakdale; Barbara Illingworth, St. Louis Park, all of Minn.; William H. Borner, Dana Point; Susan I. Montoya, San Clemente, both of Calif.

[73] Assignee: St. Jude Medical, Inc., St. Paul, Minn.

[ * ] Notice: This patent issued on a continued prosecution application filed under 37 CFR 1.53(d), and is subject to the twenty year patent term provisions of 35 U.S.C. 154(a)(2).

[21] Appl. No.: 08/695,067

[22] Filed: Jul. 31, 1996

[51] Int. Cl.[7] .......................... C07G 17/00; C07G 15/00; C14C 1/00
[52] U.S. Cl. .......................... 435/267; 435/265; 435/268
[58] Field of Search ..................... 435/265, 267, 435/268

[56] References Cited

U.S. PATENT DOCUMENTS

| | | | |
|---|---|---|---|
| 1,767,536 | 6/1930 | Le Petit | 435/265 |
| 3,318,774 | 5/1967 | Dingwall et al. | 167/74 |
| 4,553,974 | 11/1985 | Dewanjee | 8/94.11 |
| 4,776,853 | 10/1988 | Klement et al. | 8/94.11 |
| 4,801,299 | 1/1989 | Brendel et al. | 623/1 |
| 4,943,530 | 7/1990 | Christner et al. | 435/188 |
| 5,336,616 | 8/1994 | Livesey et al. | 435/240.2 |
| 5,397,353 | 3/1995 | Oliver et al. | 623/11 |
| 5,595,571 | 1/1997 | Jaffe et al. | 8/94.11 |

FOREIGN PATENT DOCUMENTS

| | | |
|---|---|---|
| 0 564 786 | 10/1993 | European Pat. Off. . |
| 42 04 132 | 8/1992 | Germany . |
| WO 95/28183 | 10/1995 | WIPO . |
| WO 96/08213 | 3/1996 | WIPO . |
| WO 96/32905 | 10/1996 | WIPO . |

OTHER PUBLICATIONS

Matsuda et al., "Application of Ubiquinone Systems and Electrophoretic Comparison of Enzymes to Identification of Clinical Isolates of Asperigillus–fumigatus and several other species of Aspergillus", J. Clin. Microbiol. 30 (8) 1999–2005 (1992).
van Gulik et al., "The processing of sheepskin for use as a dermal collagen graft—an experimental study", Netherlands Journal of Surgery 39 (3): 90–4 (1987).
ATCC Bacteria & Bacteriophages pp. 191–193 (1992).
"Cloning and expression in Bacillus subtilis of the npr gene from Bacillus thermoproteolyticus Rokko coding for the thermostable metalloprotease thermolysin", M.J. O'Donohue et al. Biochem J. vol. 300 pp. 599–603 (1994).
Barbarash et al., "Methods of Preventing Calcification of Heart Valve Bio–prostheses", Biull. Eksp. Med. (USSR) Dec. 1988 (English translation included).
Dzemeshkevich et al., "The Mitral Valve Replacement by the New–Type Bioprostheses (Features of Design and Long– Term Results)", J. Cardiovasc. Surg., vol.35, Suppl. 1 to No. 6, pp. 189–191 (1994).
Konstantinov et al., "New Cardiac Bioprostheses: Theory, Experiments, and 10 Years of Clinical Use", Ann. Thorac. Surg., vol. 48, pp. 579–580 (1989).
Malinovski, et al., "Combined Enzyme and Chemical Processing", in Biological Prostheses of the Heart Valves, Meditsina (Moscow) 1988 (English translation included).

*Primary Examiner*—Sandra E. Saucier
*Attorney, Agent, or Firm*—Westman, Champlin & Kelly, P.A.; Peter S. Dardi; Hallie A. Finucane

[57] ABSTRACT

A method is disclosed for processing tissue by inoculating the tissue with a solution having microorganisms, where the microorganisms are selected to produce compounds that process the tissue. The tissue is incubated with the inoculated microorganisms under conditions that are effective for processing the tissue by the chemicals produced by the microorganisms. The tissue may be subsequently treated to substantially remove or inactivate the microorganisms.

15 Claims, No Drawings

USE OF MICROORGANISMS FOR DECELLULARIZING BIOPROSTHETIC TISSUE

BACKGROUND OF THE INVENTION

The invention relates to a process for treating tissues using viable or nonviable cells, preferably microorganisms. More particularly, the invention relates to the use of microorganisms as an in vitro source of compositions for the processing of tissue to produce biomaterials useful in the production of bioprostheses.

Bioprostheses, i.e., bioprosthetic devices, are used to repair or replace damaged or diseased organs, tissues and other structures in humans and animals. Bioprostheses must be generally biocompatible with the recipient patient since they are typically implanted for extended periods of time. Bioprostheses can include artificial hearts, artificial heart valves, ligament repair material, vessel repair material, surgical patches constructed of mammalian tissue and the like. Considerable effort has been invested in the development of bioprosthetic heart valves, and the following discussion, for simplicity, will focus on these devices. It is to be understood, however, that the subject matter of this application is not limited to heart valves.

Currently available prostheses for the replacement of defective heart valves and other vascular structures may be classified as mechanical or bioprosthetic. Although mechanical valves have the advantage of proven durability through decades of use, they frequently are associated with a high incidence of blood clotting on or around the valve, necessitating continuous treatment with anticoagulants. Bioprosthetic heart valves constructed from materials derived from biological tissues were introduced in the early 1960's. Bioprosthetic heart valves are typically derived from porcine aortic valves or are manufactured from other biological materials such as bovine pericardium. Bioprostheses can include a combination of tissue-derived materials and synthetic materials.

A major rationale for the use of biological material for heart valves is that the profile and surface characteristics of biological material are optimal for laminar, nonturbulent flow. The result is that intravascular clotting is less likely to occur than with mechanical valves. This reduction in thrombogenicity has been well documented in clinical use of glutaraldehyde-fixed bioprosthetic valves. Glutaraldehyde fixes tissue by reacting to form covalent bonds with free amino groups in proteins, thereby chemically crosslinking nearby proteins.

Generally, bioprosthetic heart valves begin failing after about seven years following implantation, and few bioprosthetic valves remain functional after 20 years. Replacement of a degenerating valve prosthesis subjects the patient to additional surgical risk, especially in the elderly and in situations of emergency replacement. While failure of bioprostheses is a problem for patients of all ages, it is particularly pronounced in younger patients. Over fifty percent of bioprosthetic valve implants in patients under the age of 15 fail in less than five years, due to calcification.

Mineralization, e.g. calcification, appears to be the primary process leading to degeneration of bioprostheses. Efforts to address the calcification problem have included treating glutaraldehyde-fixed valves with compounds such as toluidine blue, sodium dodecyl sulfate and diphosphonate to reduce calcium nucleation. Other approaches include removal of reactive glutaraldehyde moieties from the tissue by a chemical process. Xenograft tissue, i.e., tissue from a species other than the species of the recipient patient, typically is fixed with glutaraldehyde prior to implantation to reduce the possibility of immunological rejection.

Still other approaches include development of alternative fixation techniques, since evidence suggests that the glutaraldehyde fixation process itself may contribute to calcification and mechanical deterioration. In addition, since nonviable cells present in transplanted tissue are sites for calcium deposition, investigators have developed various processes ("decellularization" processes) to remove cellular structure from the valve matrix. For example, detergents and nucleases have been used to obtain an extracellular matrix from tissue for use as graft material.

Fixation and treatment to reduce calcification generally involve harsh conditions that tend to sterilize the tissue. Absence of living microorganisms, primarily bacteria and fungi, is an important consideration for any bioprosthetic material intended for implantation into a patient since implantation of a nonsterile implant may be catastrophic for the patient. Thus, previous approaches to preparation of medical implants, including bioprostheses, generally have avoided introduction of microorganisms or, at least, have not encouraged the growth of microorganisms around and within the implant material.

SUMMARY OF THE INVENTION

In a first aspect, the invention involves a method for processing tissue including the steps of:

a) inoculating the tissue with a solution having microorganisms that are selected to produce one or more compounds effective to process the tissue; and b) incubating the tissue in the solution under conditions effective for processing the tissue by the compounds produced by the selected microorganisms. The process can include the step of treating the tissue to substantially remove or inactivate the microorganisms. Preferred tissue, prior to processing, includes cells and an extracellular matrix. The one or more compounds can include a compound effective at decellularizing the tissue while leaving the extracellular matrix substantially intact. The selected microorganisms can carry one or more exogenous genes encoding enzymes effective for decellularizing the tissue. The solution used during incubation can include an additive effective at reducing enzyme activities detrimental to the matrix.

The one or more compounds can include a replacement extracellular matrix constituent effective to reinforce an extracellular matrix within the tissue. A preferred replacement extracellular matrix constituent can be selected from the group consisting of proteoglycans, glucosaminoglycans, collagen, elastin, glycoproteins and lipoproteins. The one or more compounds can also include an antioxidant. The one or more compounds can include a surface modification chemical effective to treat the tissue. The surface modification chemical can be selected from the group consisting of heparin, RGD sequence containing peptides, fibroblast growth factors, transforming growth factors and other chemotactants. The one or more compounds can include a compound effective to crosslink proteins.

The method of the invention can further include the step of adding a growth medium effective for selecting for proliferation of desired microorganisms. The method can also further include the step of monitoring the solution to estimate numbers of the microorganisms or to determine metabolic activity of the microorganisms.

The inoculated microorganisms preferably are selected to have low levels of endotoxin. The inoculated microorganisms can be selected for susceptibility to one or more inactivating mechanisms selected from the group consisting of ionizing radiation, ultraviolet irradiation, antibiotics and chemical exposure. The selected inoculated microorganisms can carry an exogenous, inducible suicide gene, such that the processing includes inducing the suicide gene.

The selected inoculated microorganisms can produce antimicrobial agents effective for inhibiting growth of undesired microorganisms in the solution. The incubation can be performed in the presence of a media supplement effective to enhance or to inhibit specific cellular activity. The selected inoculated microorganisms preferably would be resistant to antimicrobial agents effective for inhibiting growth of undesired microorganisms.

The method of the invention can further include the step of forming a bioprosthetic article from the tissue. Preferred microorganisms include Micrococcus luteus bacteria.

In another aspect, the invention involves a method for decellularizing a tissue, the tissue including cells and an extracellular matrix, the method including the step of:

a) contacting the tissue with a solution comprising microorganisms selected to produce enzymes and other materials effective for decellularizing the tissue while leaving intact the matrix;

b) incubating the tissue in the solution under conditions effective for decellularizing the tissue while leaving intact the matrix, to form a decellularized tissue. The method can further include the step of treating the decellularized tissue to remove or inactivate the microorganisms. The decellularized tissue preferably comprises a bioprosthetic article.

In another aspect, the invention involves a method for processing a tissue, the tissue including cells and an extracellular matrix, the method including the steps of:

a) contacting the tissue with a growth medium, the tissue comprising microorganisms that produce one or more compounds effective for processing the tissue, where the growth medium is effective for selecting for proliferation of desired microorganisms;

b) incubating the tissue in the growth medium under conditions effective for processing the tissue. The method can further include the step of treating the tissue to substantially remove or inactivate the microorganisms. The tissue prior to processing preferably includes cells and an extracellular matrix such that the one or more compounds include a compound effective at decellularizing the tissue while leaving the extracellular matrix intact. The solution used during incubation can include an additive effective at reducing enzyme activities detrimental to the matrix.

The one or more compounds can include the following: enzyme inhibitors effective at inhibiting enzyme activities detrimental to the matrix, a replacement extracellular matrix constituent effective to reinforce an extracellular matrix within the tissue, an antioxidant, a surface modification chemical, an enzyme effective to crosslink proteins or a combination thereof.

In another aspect, the invention involves a method for processing a tissue, the tissue including cells and an extracellular matrix, the method including the steps of:

a) contacting the tissue with a solution comprising lysed microorganisms, where the microorganisms are selected to produce one or more compounds effective for processing the tissue; and b) incubating the tissue in the solution under conditions effective for processing the tissue. The tissue prior to processing can include cells and an extracellular matrix. The one or more compounds can include a compound effective at decellularizing the tissue while leaving the extracellular matrix intact. The solution used during incubation can include an additive effective at reducing enzyme activities detrimental to the matrix.

The one or more compounds can include one or more of the following: enzyme inhibitors effective at inhibiting enzyme activities detrimental to the matrix, a replacement extracellular matrix constituent effective to reinforce an extracellular matrix within the tissue, an antioxidant effective to reduce oxidation of the tissue, a surface modification chemical, a compound effective to crosslink proteins.

The method can further include the step of inoculating the tissue with a solution having microorganisms that are selected to produce compositions effective to process the tissue. The method can also further include the step of contacting the tissue with a growth medium effective for selecting for proliferation of desired microorganisms.

The present invention offers significant advantages with respect to processing tissue. For example, the invention provides a simple yet effective method of decellularizing tissue. Other advantages will be apparent from the further disclosure of the invention and the claims.

DETAILED DESCRIPTION OF THE INVENTION

The present invention is based on the realization that microorganisms surprisingly are useful tools for preparing bioprosthetic tissue. Specifically, microorganisms can be useful for processing or treating the tissue, for example, by decellularizing the tissue, by preventing unwanted deterioration of the extracellular matrix or by improving the qualities of the tissue. Microbial-induced improvement in the quality of the tissue could involve modifications to almost any feature of the tissue. The microorganisms can be viable or non-viable.

Microorganisms are selected for specific bioactivities. For example, microorganisms may be selected for ability to degrade nucleic acid polymers. Conversely, microorganisms that degrade necessary structural components such as collagen and elastin should be avoided. Other possible characteristics of desired microorganisms are discussed below.

The processes of the invention are useful for treating various tissue types including heart valves, aortic roots, walls, or leaflets, vascular grafts, pericardial tissue such as pericardial patches, tendons, ligaments, dura mater, skin preparations, cartilage, fascia, homograft tissue, bypass grafts, blood vessels, human umbilical tissue, bone, or any other tissue where modification is desirable. The tissue can be from a human or from other species, such as porcine, bovine, seal and kangaroo tissues. Such natural tissues are typically composed of collagen and elastin matrices with cells dispersed throughout the matrix. The tissue can also include tissue synthetic material, which involves a repopulated, resorbable matrix which forms a synthetic tissue.

Tissues treated using the processes of this invention may be used in a variety of bioprostheses including those directed to cardiovascular, orthopedic, gastrointestinal or other applications. The present invention is particularly appropriate for medically related uses. However, non-medical uses for the invention, such as processing of leather, are also possible.

In the context of the invention, microorganisms include procaryotic cells, eukaryotic cells and mixtures thereof. Microorganisms of particular interest include fungi, yeast, bacteria and cultures of cells from multicellular organisms. The microorganisms can be genetic wild types, mutants or genetically engineered organisms.

With respect to decellularization, microorganisms represent sources of digestive enzymes and possibly other products effective in removing cellular structure from the tissue matrix to be used in the bioprosthesis. The present invention involves controlled decellularization with viable, nonviable or lysed microorganisms. The microbial decellularization preferably leaves the extracellular matrix substantially intact. Microorganism-based decellularization is efficient, highly effective and relatively inexpensive.

Microorganisms are known to produce various enzymes including nucleases, proteases and phospholipases. Production and release of these enzymes can result in digestion of surrounding material to produce an array of substituents, for example nutrients that can be ingested by the microorganisms. Commercially available enzymes are typically isolated from cultures of microorganisms. Decellularization obtained by contacting tissue with, among other compounds, certain categories of purified enzymes is disclosed, for example, in U.S. patent application Ser. No. 08/424,218, incorporated herein by reference.

The invention offers distinct advantages over the enzyme incubation methods of decellularization. The present invention eliminates the need to isolate the enzymes and offers the possibility of decellularization using a wider range of digestive enzymes and possibly other compounds without isolation or even identification of the pertinent compounds. Additionally, with the elimination of the requirement to isolate and purify enzymes, significant cost savings are achievable.

Microorganisms can be useful in performing other processing functions beyond decellularization. For example, the microorganisms can be used to preserve the integrity of the tissue. To serve this function, the microorganisms can be selected to produce antibiotics to retard the growth of undesirable microorganisms that would contaminate or damage the tissue. Alternatively, the microorganisms can be selected to secrete antioxidants, such as vitamin E or carotinoids, to mitigate against oxidative damage to the extracellular matrix due to chemicals or radiation. The microorganisms similarly can be selected to produce inhibitors of collagenase and/or elastase, enzymes that can degrade the extracellular matrix.

In addition, microorganisms can perform constructive processing of the tissue. For example, the selected microorganisms can produce replacement extracellular matrix constituents, such as complex proteoglycans, simpler glucosaminoglycans, collagen, elastin, glycoproteins and lipoproteins. The microorganisms can produce other desirable surface modifying chemicals. Appropriate surface modifying chemicals include heparin, which modifies thrombogenicity, and other chemicals that modify healing responses, such as fibronectin, other arginine-glycine-aspartic acid (RGD) sequence-containing peptides, fibroblast growth factors, transforming growth factors and other chemotactants.

Other examples of constructive processing involve microorganisms that produce enzymes effective at crosslinking the extracellular matrix. While these crosslinking enzymes are oxidative in nature, they can be less toxic than current chemical crosslinking methods.

In one embodiment, the invention entails the use of a selective growth medium that promotes growth, maintenance or metabolic activity of particularly useful microorganisms and/or that correspondingly inhibits other microorganisms. In an alternative embodiment, the tissue is inoculated with one or more selected types of microorganisms chosen for the ability to decellularize or otherwise process the tissue. A further alternative embodiment involves culturing microorganisms selected for desirable characteristics, then lysing the cells to release the enzymes and other cellular constituents. Subsequently, the released constituents, in the form of a crude lysate, filtered lysate (filtrate) or purified preparation, is added to the tissue sample. In any of the embodiments, the solution containing the microorganisms can be monitored to estimate the number of microorganisms or to determine the metabolic activity of the microorganisms.

Selective Growth Medium

Addition of simple saline or buffer to the tissue allows for growth of an unspecified range of microorganisms. Under these non-specific conditions, the characteristics of the microorganism population will depend on the species/strains and numbers present initially in the tissue, e.g., the extent and nature of contamination of the tissue upon receipt. Populations also will vary depending on nutrients and other substances present and released by cells in the tissue matrix. Presumably, these "non-selected" organisms survive and proliferate by consuming materials from the dying tissue cells as nutrients. This may or may not involve some minimal and effectively unspecific selection process based on competition among microorganisms for unspecified nutrients and other factors in this environment.

In contrast, a selective growth medium of the present invention favors those microorganisms selected to be particularly useful for effective tissue processing. Furthermore, use of a specific growth media can be used to induce production of useful enzymes by the microorganisms (e.g., phospholipases and nucleases) and/or suppress production of deleterious enzymes (e.g., collagenase and elastase).

Examples of growth promoting molecules useful in the selective growth media of the present invention include RNA, DNA, lipids, carbohydrates, proteins and other selected carbon sources. A selective growth medium can be designed also to inhibit the growth of undesired microorganisms such as those producing toxins or those capable of competing with the favored microorganisms. Examples of selective growth inhibitors include antibiotics such as neomycin, streptomycin, penicillin, gentamicin, Amphotericin B, and other compounds capable of selectively inhibiting the growth of microorganisms. Additionally, a media supplement can be added to enhance or to inhibit specific cellular activity, such as promotion, transcription, translation and expression of gene products. The growth media can include additives effective to reduce specific enzyme activities, detrimental to the extracellular matrix.

These components can be added individually or in combinations to aqueous solutions along with salts and/or buffering compounds to form the growth medium. Alternatively, commercially available media can be supplemented with appropriate components.

Inoculation

In this embodiment, the medium surrounding the tissue and/or the tissue itself is inoculated with a selected microorganism or combination of microorganisms. An inoculated medium in which the tissue is incubated can be a simple saline/buffered solution. Alternatively, more complex growth media can be used to allow growth of the inoculated microorganisms and/or to inhibit some or all of the natural contaminating microorganisms. Inoculation can occur before or after the tissue is placed in the medium. The numbers of microorganisms inoculated per heart valve or other bioprosthesis will depend on the microorganism type and its growth curve. For example, we have found inoculation with about $10^6$ cells of *Micrococcus luteus* per valve to be useful in decellularization.

The inoculated organisms may out-compete the naturally occurring microorganisms either because of an initially large inoculum or because of rapid proliferation due to genetic advantages and/or environmental factors. Relatively large initial inocula reduce the time needed to create an effective population of microorganisms. If necessary, additional inocula can be administered during the incubation period, as desired.

Inoculated microorganisms are selected to produce appropriate constituents to process the tissue as desired. Furthermore, selected microorganisms should produce at most low levels of toxins potentially harmful to a patient receiving the bioprosthesis and low levels of proteolytic enzymes that can degrade the collagen and elastin in the extracellular matrix. Preferably, the selected microorganisms are susceptible to inactivation either by exposure to radiation such as ionizing radiation (including x-rays, gamma rays and beta rays) and ultraviolet light, or by chemical methods. For example, microorganisms lacking cell coats are particularly suited to inactivation by external agents.

In one embodiment, the microorganisms are genetically engineered to be more effective at processing the tissue, more effective at out-competing the endogenous microorganisms, or more easily eliminated when the processing is completed. For example, microorganisms can be engineered to produce relatively large amounts of desirable enzymes, such as phospholipase, lipase, DNAse, RNAse and prolyl-hydroxylase. Similarly, the microorganisms can be engineered to express enzymes that the corresponding wild type organisms do not produce.

In order to out-compete undesirable contaminating microorganisms, the inoculated microorganisms can be genetically engineered or naturally selected for resistance to one or more antibiotics or other biocidal compositions. The growth medium then can be supplemented with the appropriate biocidal compositions, or the inoculated microorganisms can be engineered or selected to produce the biocidal compositions themselves. Introduction of biocidal resistance into microorganisms is a standard selection procedure in the genetic engineering of microorganisms.

To reduce bioburden and to facilitate eventual sterilization, the organism can be genetically engineered to possess a "suicide gene" construct. Such constructs are designed to activate transcription of a suicide gene when certain activating stimuli are received by the organism. Upon receiving the stimulus, the suicide gene is expressed, which leads to death of the cell. Examples of suitable suicide genes include the so-called hok, gef and relF genes. The expression of these genes can be triggered, for example, by introduction of isopropyl-thiogalactosidase into the medium if a lac promoter is used, or removal of tryptophan from the medium if a trp promoter is used. Other suicide gene promoters can be activated, for example, by lactose, lycine or any other appropriate amino acid. A general discussion of suicide genes useful for inactivation of bacteria can be found in S. Molin et al., Suicide Genetic Elements and Their Use in Biological Containment of Bacteria, Ann. Rev. Microbiol. 47:139–166 (1993).

One or more of the above-described features, whether or not genetically engineered, can be combined within a single organism. Furthermore, in appropriate settings, it can be useful to mix a plurality of types of microorganisms with different genetically engineered or wild type characteristics, particularly when the characteristics of individual members of the mix are known to provide specific, desirable processing of the tissue.

Lysed Microorganisms

Lysed cells can provide a source of enzymes and other materials effective for decellularization. Selected microorganisms are grown in vitro in the absence of any bioprosthetic tissue. After a desired cell density is reached, the cells are lysed. For example, cells can be lysed by sonication, by the addition of lysozyme or other methods of lysis. Preferably, the solution of lysed cells is sterile filtered to remove remaining viable cells, membrane fragments and other cellular substructure that could complicate tissue processing, for example, by encouraging growth of undesired microorganisms.

The filtered solution can be further concentrated or fractionated if desired. Multiple solutions from culturing of different microorganisms can be mixed either before or upon addition to the tissue. Alternatively, the solutions can be added sequentially if it is necessary to control the phases and timing of the processing process in a particular bioprosthetic tissue.

Combinations of Processes

It can be useful to combine two or more embodiments described above. For example, the selective growth medium may contain nutrients to encourage growth of certain microorganisms found naturally in freshly harvested tissue, while the tissue also is inoculated with selected microorganisms whose growth similarly is encouraged by the growth medium. The combined growth of microorganisms may be more effective than either approach separately because of the correspondingly wider array of processing abilities of the different microorganisms. The third embodiment using a cell filtrate can be combined with either or both of the first two embodiments. In this way, the digestive products contributed by the cell filtrate can supplement any deficiencies in the processing ability of the growing microorganisms.

When a bioprosthetic tissue is subjected to more than one of the above-described embodiments of the invention, the treatments may take place concurrently or sequentially, as desired, to obtain the most rapid and complete processing.

Additional Processing

Additional treatments can be used to supplement the microbial-based treatments. For example, one can treat the tissue with hypertonic and/or hypotonic solutions to lyse endogenous cells in order to provide for more efficient digestion by the enzymatic secretions of the microorganisms. See, e.g., U.S. patent application Ser. No. 08/424,218, referenced above. Additional purified enzymes can supplement the digestive abilities of the microorganisms. Similarly, other useful compositions, including without limitation crosslinking agents, surface modification compositions, antioxidants and extracellular matrix components, can be added to the tissue. Specifically, the tissues can be further treated by a crosslinking agent such as glutaraldehyde.

In the production of bioprostheses, sterilization of the final product is a significant issue. Furthermore, contamination of the sterilized bioprosthesis by excessive numbers of dead microorganisms may have a deleterious effect on biocompatibility with the recipient patient. With regard to both sterilization and biocompatibility of the finished device, both type and number of microorganisms are important. For example, *Bacillus subtilis* spores are particularly resistant to sterilization, and high concentrations of gram negative bacteria may increase endotoxin levels.

As noted above, the present invention can involve controlled microbial growth. The control can take several forms. First, the growth medium can be adjusted to limit the growth of unwanted organisms. In addition, encouraging growth of desirable microorganisms limits growth of undesired microorganisms through competition. Generally, knowledge of the characteristics of the major microbial burden permits efficient treatment and evaluation of success at decontamination.

Bioburden reduction and/or sterilization can be accomplished in a variety of ways. If the organisms have been selected or genetically engineered to die in response to particular conditions, the conditions can be invoked to kill off the organisms. For example, activators of particular suicide gene constructs may be added to the medium surrounding the bioprosthetic tissue. Subsequent processing can be used to remove the microorganisms and other material associated with the microbes that could be deleterious, such as endotoxins or liposaccharides. For example, microorganisms can be removed by soaking, rinsing or filtration.

Furthermore, the tissues may be recolonized with viable cells compatible with the ultimate recipient. The recolonization can take place either in vitro by cell culture or in vivo after implantation.

Example

The experiments presented in this example demonstrate the effectiveness of microorganisms as facilitators of decellularization. Experiments were conducted on porcine aortic valves.

Investigators have observed that heart valve tissues left in plain or buffered saline at 25° C. may undergo a "decellularization" process without any additional intervention. By characterizing the microbial flora in these studies, it was determined that several types of organisms seemed to be present when decellularization took place. In other words, natural contaminating bacteria were isolated and characterized for instances where decellularization occurred and correlation analysis was conducted to determine which organisms had a higher probability for involvement in the decellularization. Three different species of bacteria were selected for further study: *Micrococcus luterus* (A), *Shewanella* (Pseudomonas) *pitrefariens* (B), and *Staphylococcus epidermidis* (C).

To prepare the inoculum for the present study, the selected bacteria were heavily streaked onto six Trytic Soy Agar (TSA) plates per organism without any expectation of getting individual colonies. The inoculated TSA plates were incubated for 24 hours at 28–35° C. (A and C) or 20–25° C. (B).

To prepare a liquid inoculum, the bacteria were harvested from the agar surface of all the plates using sterile 0.05 M citrate-buffered, physiological-saline solution (CBS) prepared using 7.5 g NaCl, 3.6 g $Na_2PO_4$, 0.27 g $H_3C_6H_5O_7H_2O$ in one liter of water adjusted to pH 7.4. The saline solution previously had been sterilized by steam autoclaving for 35 minutes at 250° C. The inoculum was made as concentrated as possible, using the minimum volume of solution necessary to suspend the cells. Approximately, 5.5 ml of inoculum were recovered from each plate for a total of 33 ml for each organism combined into a single tube. Each tube of inoculum was mixed using a vortex mixer to disperse clumps and attain approximate homogeneity. The inoculum was made prior to preparing the porcine valves for the decellularization study.

The inoculum concentration was determined by the pour plate method using serial dilutions. The pour plate method involves a series of 1:10 dilutions with CBS staring with 1.0 ml of homogeneous inoculum. The dilutions were continued until an appropriate series of dilutions was produced.

Duplicate pour plates (TSA) were inoculated with one diluted inoculum each covering an appropriate range of dilutions such that one plate would be expected to have between 30 and 300 colony forming units (CFU). The pour plate enumeration results for the inocula were as follows:

*Micrococcus luteus*—$10^{-7}$ dilution
   Plate 1–103 colonies
   Plate 2–149 colonies
   Average=$1.26\times10^9$ CFU/ml
*Shewanella putrefaciens*—$10^{-8}$ dilution
   Plate 1–135 colonies
   Plate 2–115 colonies
   Average=$1.25\times10^{10}$ CFU/ml
*Staphylococcus epidermidis*—$10^{-8}$ dilution
   Plate 1–38 colonies
   Plate 2–43 colonies
   Average=$4.1\times10^9$ CFU/ml Similarly, the bioburdens of the valves at the start of the study were determined. Valves were obtained from standard suppliers, which slaughter the animals under USDA prescribed conditions. Processing of the valves takes place within 96 hours of slaughter. Two valves from each of two tissue batches individually were placed in 100 ml diluting CBS fluid and shaken for ten minutes. Three 1:10 serial dilutions were made from the decanted diluting fluid. TSA pour plates were inoculated with the resulting solutions and incubated at 30° to 35° C.

The first sample from Batch 1 had a bioburden of $8.8\times10^3$ CFU per gram of valve tissue while the second sample had a bioburden of $8.2\times10^3$ CFU/g. The average CFU per Batch 1 valve was $1.6\times10^5$. Seven different colony morphologies were observed upon plating out the microorganisms from the Batch 1 valves. The first sample from Batch 2 had a bioburden of $6.2\times10^2$ CFU/g while the second sample had a bioburden of $5.9\times10^2$ CFU/g. The average CFU per Batch 2 valve was $1.6\times10^4$. Six different colony morphologies were observed upon plating out the microorganisms from the Batch 2 valves.

For the decellularization study, on the same day that the porcine valves were received, the valves were rinsed in sterile CBS solution. The rinsed valves then were placed in sterilized 600 ml beakers, two valves per beaker. A total of 18 beakers were prepared. Six beakers were used for each of the three microorganisms. Nine beakers had valves from the Batch 1 while the other nine had valves from Batch 2. Therefore, three beakers with valves from the same source were inoculated with each microorganism. The three beakers prepared in the equivalent way were incubated for different amounts of time, as described below.

The weights of the two porcine valves in the beakers ranged from 69.3 to 105.5 g for the Batch 1 valves and 49.1 to 72.1 for the Batch 2 valves. The volume of inoculum for each species of bacteria was equally divided into six quantities so that each beaker received about the same quantity of inoculation. About 395 mls of CBS were added to each beaker followed by the about 5 ml of the appropriate inoculum. The beakers then were covered with parafilm and briefly swirled by hand. The covered beakers were incubated at 20 to 25° C., i.e. room temperature.

One third of the beakers were selected for incubation for 24 hours, another third for 48 hours and the final third for 72 hours. A 5 to 10 ml portion of solution was removed from each beaker to determine the microbial concentration using the pour plate method after brief storage in a refrigerator. The remaining solution was removed, and the valves were rinsed twice in sterile CBS. The valves were transferred to a new sterile beaker and then placed in 400 ml of CBS with 0.2 percent glutaraldehyde for seven days. The valves were later fixed in 2 percent glutaraldehyde and sectioned for histological examination.

To perform the pour plate enumeration on the test samples following incubation, the samples were first mixed well using a vortex mixer. Then, serial dilutions were performed as described above. The plates were then incubated at the appropriate temperature for the specific organism. The average results are presented in the following table.

| SAMPLE | 24 HOURS CFU/ml | 48 HOURS CFU/ml | 72 HOURS CFU/ml |
| --- | --- | --- | --- |
| Batch 1-A | $2.0 \times 10^7$ | $1.8 \times 10^7$ | $2.7 \times 10^8$ |
| Batch 2-A | $3.0 \times 10^7$ | $1.11 \times 10^8$ | $2.9 \times 10^8$ |
| Batch 1-B | $5.6 \times 10^7$ | $9.0 \times 10^7$ | $2.6 \times 10^8$ |
| Batch 2-B | $1.2 \times 10^8$ | $5.5 \times 10^6$ | $2.2 \times 10^8$ |
| Batch 1-C | $2.7 \times 10^7$ | $1.14 \times 10^8$ | $1.5 \times 10^8$ |
| Batch 2-C | $3.5 \times 10^7$ | $6.6 \times 10^7$ | $2.8 \times 10^8$ |

After 24 hours, cultures from Batch 1 samples produced colonies where between about 87 percent and about 98 percent of the colonies had the same morphology. In contrast, cultures from the Batch 2 sample after 24 hours produced colonies where the largest group of colonies with the same morphology included between about 40 percent and about 90 percent of the colonies. This indicated likely contamination in the Batch 2 sample by nonselected microorganisms.

After 48 hours, the Batch 1 samples produced colonies where a maximum of between 40 percent and 70 percent of the colonies had the same morphology compared with a maximum of 50 and 80 percent for the Batch 2 sample. The 48 hour results show similar homogeneity of microorganisms from the Batch 1 and Batch 2 samples. After 72 hours, the Batch 1 samples again produced a more homogeneous culture with between 70 and 90 percent of colonies having the same morphology compared with a maximum of 40 to 70 percent of the cultures having the same morphology for the Batch 2 sample.

With respect to the physical appearance of the samples, 24 hours after inoculation with microorganism A, the Batch 1 tissue sample was darker and redder than the Batch 2 sample. The solution from the Batch 2 sample had a yellowish tinge. In general, both solutions were darker and murkier looking than the four other solutions incubated with specimens inoculated with microorganisms B and C. The tissues inoculated with microorganism A seem to have been digested to a greater extent than the other four tissue samples. The tissues incubated with microorganisms B or C were relatively fresh looking. Visually, the type of organism had a distinctive effect on the heart valve tissue, possibly indicating the degree or speed at which decellularization is taking place.

Forty-eight hours after inoculation with microorganism A, the tissue had a grayish dark color while the solution was very murky with a greenish brown tinge. The tissue inoculated with microorganism B had a grayish color, and the solution had a pinkish tinge and was less murky than the solutions inoculated with microorganism A. The tissues inoculated with microorganism C had a more pinkish tinge and looked fresher while the corresponding solution was more reddish and less murky. The appearances of the tissue and the solutions were more dependent on the type of inoculated microorganism than on the tissue source.

After 72 hours, all the solutions were very murky. The two solutions inoculated with microorganism A had a yellowish tinge while the other four solutions were more dark red in color. All samples, before being disturbed, had a whitish scum on the liquid surface. All the myocardial muscles of the six valves appeared grey and limp after 72 hours of incubation.

To perform the histological examinations, two leaflets from each valve was excised following fixation and stained with Hemotoxylin & Eosin (H&E) stain. Each leaflet was then evaluated for cellularity which is indicated most prevalently by the presence of the cell nucleus. The following table indicates the approximate percentage of leaflets from each test group displaying a general absence of cellularity.

| SAMPLE | 24 HOURS | 48 HOURS | 72 HOURS |
| --- | --- | --- | --- |
| | Number of leaflets decellularized | | |
| Batch 1-A | 0 | 2 | 4 |
| Batch 2-A | 0 | 0 | 4 |
| Batch 1-B | 0 | 0 | 2 |
| Batch 2-B | 0 | 0 | 0 |
| Batch 1-C | 0 | 0 | 0 |
| Batch 2-C | 0 | 0 | 4 |

These results indicate that while all of the organisms displayed the ability to decellularize tissue, it is evident that *Micrococcus luteus* is more effective.

Processing of comparable tissues, not inoculated with favorable organisms or incubated in selective media, relies on variable incoming microbial populations and can exhibit slower decellularization, matrix degradation and toxin production.

What is claimed is:

1. A method for decellularizing a tissue which includes cells and an extracellular collagen matrix comprising:

a) contacting said tissue with a solution comprising viable microorganisms which are capable of decellularizing said tissue while leaving said matrix substantially intact;

b) incubating said tissue with said microorganisms under conditions effective for decellularizing said tissue while leaving said matrix substantially intact to form a decellularized tissue matrix; and c) treating said tissue matrix to substantially remove or inactivate said microorganisms, where said tissue is suitable for use in a bioprosthesis.

2. The method of claim 1, wherein said microorganisms express one or more exogenous genes encoding enzymes effective for decellularizing said tissue.

3. The method of claim 1, wherein said solution includes an additive effective at reducing enzyme activities detrimental to said matrix.

4. The method of claim 1, further comprising adding a growth medium effective for selecting for proliferation of desired microorganisms.

5. The method of claim 1, further comprising monitoring said solution to estimate numbers of said microorganisms or to determine metabolic activity of said microorganisms.

6. The method of claim 1, wherein said microorganisms have low levels of endotoxin.

7. The method of claim 1, wherein said microorganisms have a susceptibility to one or more inactivating mechanisms selected from the group consisting of ionizing radiation, ultraviolet irradiation, antibiotics and chemical exposure.

8. The method of claim 1, wherein said microorganisms express an exogenous, inducible suicide gene, and said processing comprises inducing said suicide gene.

9. The method of claim 1, wherein said microorganisms produce anti-microbial agents effective for inhibiting growth of undesired microorganisms in said solution.

10. The method of claim 1, wherein said incubation is performed in the presence of a media supplement effective to enhance or to inhibit specific cellular activity.

11. The method of claim 1, wherein said microorganisms are resistant to antimicrobial agents effective for inhibiting growth of undesired microorganisms.

12. The method of claim 1, further comprising the step of forming a bioprosthetic article from said tissue.

13. The method of claim 1, wherein said microorganisms comprise *Micrococcus luteus* bacteria.

14. The method of claim 1, wherein said microorganisms comprise *Shewanella pitrefariens* bacteria.

15. The method of claim 1, wherein said microorganisms comprise *Staphylococcus epidermidis* bacteria.

* * * * *

UNITED STATES PATENT AND TRADEMARK OFFICE
CERTIFICATE OF CORRECTION

PATENT NO. : 6,121,041
DATED : Sept. 19, 2000
INVENTOR(S) : Mirsch, II et all

It is certified that error appears in the above-identified patent and that said Letters Patent is hereby corrected as shown below:

Under [54] TITLE:
Change "DECELLULARIZING" to --PROCESSING--.

Signed and Sealed this

Fifteenth Day of May, 2001

Attest:

NICHOLAS P. GODICI

*Attesting Officer*      *Acting Director of the United States Patent and Trademark Office*